United States Patent [19]
Eyal et al.

[11] Patent Number: 5,859,262
[45] Date of Patent: Jan. 12, 1999

[54] PROCESS FOR THE PRODUCTION OF ERYTHORBIC ACID

[75] Inventors: Aharon Meir Eyal; Asher Vitner; Tal Reuveni; Betty Hazan, all of Jerusalem, Israel

[73] Assignee: Yissum Research Development Company, Israel

[21] Appl. No.: 980,092

[22] Filed: Nov. 26, 1997

[30] Foreign Application Priority Data

Dec. 1, 1996 [IL] Israel ......................................... 119731

[51] Int. Cl.$^6$ .............................. C12P 17/04; C12P 7/58; C07D 305/12; C07C 51/42
[52] U.S. Cl. .......................... 549/315; 210/650; 210/651; 210/660; 210/663; 210/669; 210/692; 435/126; 435/137; 435/806; 519/317; 514/474; 562/580
[58] Field of Search .................................... 435/126, 137, 435/503; 562/580; 549/315, 317; 514/474; 210/650, 651, 660, 663, 669, 692

[56] References Cited

U.S. PATENT DOCUMENTS

| | | | |
|---|---|---|---|
| 2,443,583 | 7/1948 | Mottern et al. | 260/344.5 |
| 3,052,609 | 9/1962 | Takahashi | 195/36 |
| 4,323,702 | 4/1982 | Kawabata et al. | 562/485 |
| 4,720,579 | 1/1988 | Kulprathipanja | 562/580 |
| 4,851,573 | 7/1989 | Kulprathipanja | 562/580 |
| 5,068,418 | 11/1991 | Kulprathipanja et al. | 562/580 |
| 5,068,419 | 11/1991 | Kulprathipanja et al. | 562/580 |
| 5,079,153 | 1/1992 | Enomoto et al. | 435/126 |
| 5,352,825 | 10/1994 | Felman et al. | 562/580 |
| 5,391,770 | 2/1995 | Le Fur et al. | 549/315 |
| 5,449,824 | 9/1995 | Felman et al. | 562/580 |
| 5,457,214 | 10/1995 | O'Donnell | 549/315 |
| 5,681,728 | 10/1997 | Miao | 210/659 |
| 5,792,631 | 8/1998 | Running | 435/137 |

FOREIGN PATENT DOCUMENTS

| | | |
|---|---|---|
| 40-21767 | 9/1940 | Japan . |
| 40-27054 | 11/1940 | Japan . |
| WO92/16490 | 10/1992 | WIPO . |
| WO93/06226 | 4/1993 | WIPO . |

OTHER PUBLICATIONS

Shimizu et al., "Studies on Erythorbic Acid Production by Fermentation Part II. Erthorbic Acid Production by Jar Fermentor," Agr. Biol. Chem., vol. 31, No. 3, pp. 346–352 (1967).

Gustafson et al., "Basicities of Weak Base Ion Exchange Resins," Ind. Eng. Chem. Fundam., vol. 9, No. 2, pp. 221–229 (1970).

Nagasawa et al., "Studies in polyelectrolytes. XLII. Dissociation equilibrium of weak–electrolytic anion–exchange resin," Mem. Fac. Eng. Nagoya Univ., vol. 10, pp. 105–111 (abstract) (1958).

Takahashi, "Erythorbic Acid Fermentation," Biotech. and Bioeng., vol XI, Issue 6, pp. 1157–1171 (1969).

Yagi et al., "Studies on Erythorbic Acid Production by Fermentation Part I. Erythorbic Acid–Producing Strain and Cultural Condition," Agr. Biol. Chem., vol. 31, No. 3, pp. 340–345 (1967).

*Primary Examiner*—Herbert J. Lilling
*Attorney, Agent, or Firm*—Arnold, White & Durkee

[57] ABSTRACT

The invention provides a process for the recovery of erythorbic acid from an aqueous feed solution containing values of erythorbic acid at a concentration of less than 0.7 mol/kg, comprising adsorbing a major portion of said erythorbic acid with a solid phase adsorbent resin selected from resins carrying a pyridine function and resins of similar or weaker basicity; separating said erythorbic acid-containing resin from residual aqueous solution, and subjecting said erythorbic acid-containing resin to a desorbing operation with a neutral solvent at a temperature of at least 20° C. higher than the temperature at which said adsorption is carried out, whereby there is obtained a solution of erythorbic acid in solvent in which the concentration of erythorbic acid is at least equal to its concentration in said aqueous feed solution.

22 Claims, 1 Drawing Sheet

PROCESS FOR THE PRODUCTION OF ERYTHORBIC ACID

The present invention relates to a process for the production of erythorbic acid. More particularly, the present invention relates to the recovery of erythorbic acid from aqueous solutions containing values of erythorbic acid in low concentrations, the term values of erythorbic acid as used herein referring to erythorbic acid, salts thereof, derivatives thereof and mixtures thereof.

Erythorbic acid is an isomer of ascorbic acid and is also named isoascorbic acid and D-araboascorbic acid. This acid and its salts (erythorbates) are widely used as alternatives to ascorbic acid and its salts in non-Vitamin C products. Erythorbates traditionally have two functions. First they act as antioxidants, controlling color and flavor deterioration in many foods, and as antimicrobial agents for foods. Secondly, erythorbates are used as meat-curing accelerators, speeding and controlling the nitrite-curing reaction, while prolonging color and shelf-life. Erythorbates therefore have many uses in the food industry and are used in conjunction with such comestibles as meat, fish, poultry, beverages, fruits and vegetables.

Takeshi Takahashi's U.S. Pat. No. 3,052,609 assigned to Sankyo Co., teaches a process for the production of D-araboascorbic acid which comprises subjecting one or more substances selected from the group consisting of D-glucose, D-gluconic acid, D-glucono-y-lactone, D-glucono-8-lactone, sucrose, maltose and starch to the action of an enzyme of a microorganism selected from the group consisting of *Penicillium decumbens, Penicillium chrysogenum, Penicillium chrysogenum* mut. fulvescens Takashima, Arima and Abe, *Penicillium meleagrinum, Penicillium cyaneofulvum* and *Penicillium notatum* in the presence of oxygen and recovering the D-araboascorbic acid which is formed.

In carrying out the process according to that invention, both a direct fermentation method and a cell suspension process may be applied.

In carrying out the direct fermentation method, too low concentration of the carbon source would result in decreased conversion to the product due to consumption of the source for the propagation of the cells. Too high concentrations would lead to lower yield due to greater conversion to byproducts and to a larger amount of residual sugar. It is preferable to use a concentration between 0.5 and 10%. It is also preferred to keep the concentration between about 0.5 and 1.0% by continuously adding the material. Other substances present in the medium are organic or inorganic assimilable nitrogen sources, mineral salts and a trace of various metals. pH is usually maintained between about 3 and 7. The time required for the fermentation is from 5 to 10 days in the case of surface culture and from 3 to 7 days in the case of submerged culture. The preferred temperature in the fermentation is 26° to 28° C.

Production of D-araboascorbic acid using the intact cell or dried cell preparation is effected in a buffer solution having a pH of about 4.0 to 6.0. The concentration of the carbon source is 0.5 to 10%, the temperature between 35° and 30° C. and the time is between 50 to 80 hours. The substrate is preferably added in intervals to keep its concentration between 0.5 and 1.0%.

The isolation of D-araboascorbic acid may be performed by first removing the mycelium by means of filtration or by means of a centrifugal procedure and subsequently applying the known procedures for isolating L-araboascorbic acid to the filtrate or supernatant. For example, an adequate amount of barium acetate is added to remove phosphates and sulfates and organic impurities are removed by treatment with active charcoal, followed by adsorption of the desired product on anion-exchange resin such as Amberlite IR4B and elution with aqueous hydrochloric acid. Furthermore, impurities are removed by means of a small amount of active charcoal and butanol and D-araboascorbic acid is crystallized by concentration in vacuum at low temperature under carbon dioxide, followed by recrystallization from solvent such as acetone or ethanolligroin.

The product concentrations, g/l, (and fermentation pH and duration) in Examples 1 to 7 of said US patent are respectively: 0.5–1.2 (pH=5–6, 7 days), 2–3 (pH=5, 3 days), 4.2 (pH=5.6, 4 days), 5.3 (pH=5.3, 5 days), 5 (pH=5.6, 10 days), 1.4 (pH=5, 4 days), 10.3 (5.0 for the initial 20 hours and about 4.0 for the remaining 40 hours).

In Examples 1 to 6 the culture filtrate, after treatment with 1 g. of barium acetate and 0.1 g. of active charcoal, is adsorbed on ion-exchange resin IR-4B, followed by elution with 1 liter of 1N-HCl. About 70% of the total content of the desired product is eluted in fractions in volume of 200–300 ml. after initiation of the elution. These fractions are shaken with butanol and, after addition of a small amount of active charcoal, are filtered to give an almost colorless transparent liquor, which is concentrated to near dryness in vacuum at temperature below 30° C. under $CO_{2-}$, followed by several concentrations in the presence of ethanol to remove most of the water. The oily substance thus obtained is allowed to stand in a vacuum desiccator for 2–3 days to separate crystalline D-araboascorbic acid.

In Examples 7 and 8, after completion of the reaction, pH is adjusted to 2.0 with $H_2SO_4$ and the mycelium is separated by filtration. The filtrate is treated with about 1 g. of barium acetate and about 0.1 g. of active charcoal per liter followed by filtration. The filtrate is passed through ion-exchange resin IR-4B pretreated with acetic acid to adsorb D-araboascorbic acid contained in the filtrate. The ion-exchange resin column is treated with 1N-HCl and about 70% of the total content is eluted in 200–300 ml. of the first fractions from the elution. The eluate, after addition of a small amount of active charcoal, is filtered to give almost colorless transparent solution. The solution is concentrated to near dryness in vacuum under $CO_2$ Repeated concentrations after addition of ethanol to the residue give an oily substance almost water free. The oily substance thus obtained is concentrated in vacuum to give crystalline D-araboascorbic acid.

The recovery yield shown in examples 3 to 8 were low, 19, 23, 20, 29, 29 and 28%, respectively. A possible explanation for that is the presence of HCl in the eluate. On concentration of the latter, HCl could cause decomposition of the product. Another disadvantage of the recovery process is the high consumption of acids and bases and the resulting formation of by-product salts.

Seven years after said US patent was granted, the inventor issued an article entitled: Erythorbic acid fermentation, which was published in Biotechnology and Bioengineering Vol. XI, pages 1157–1171 (1969). (Takahashi had several earlier publications, see references in the 1969 article.) Two other related publications, by Yagi and co-workers and by Shimizu and co-workers, respectively are: Studies on Erythorbic acid production by fermentation, Part I, Erythorbic acid producing strain and cultural conditions and Part II, Erythorbic acid production by jar fermentors, published in Agr. Biol. Chem. Vol. 31, pages 340–345 and 346–352, respectively (1967). These articles describe studies directed to development of an industrial process including strain improvement, optimization of culture solution (carbon source, nitrogen source, additives, effects of iron and copper and of chelating agents), temperature, aeration and agitation.

Glucose and sucrose were found to be the most appropriate carbon source. Glucose concentration should be in the range of 8–12%. In one test the fermentation was started with 8% glucose, 8% glucose was fed on the third day and 4% glucose was fed on the sixth day. The yield in that case amounted to about 40% of the total glucose supplied. The erythorbic acid concentration in the solution reached 80 g/l. The preferred temperature is about 30° C.

In the course of typical fermentations the pH of the broth is gradually lowered along the consumption of sugar and remains in the range of 3.8–4.5. Erythorbic acid production reaches maximum yield at 5–7 days.

Working with washed cells at lower glucose concentrations show higher yields. In a test comparing fermentations starting with 1, 2 and 3% glucose (at 29° C.), the following yields were found after 48 hours: about 80, 65 and 38% respectively. The initial pH was 5, decreasing to 4.0–4.3 at the end.

The broth was clarified by separation of the mycelia, and by successive filtration after addition of Ba(OH)$_2$ and treated with active carbon and a strong acid cation exchanger, Duolite C-20 in acid form. Then it was treated with a weak base anion exchanger, Amberlite IR45, in free base or acetate form, which adsorbed the erythorbic acid. The resin was then washed with water and eluted with 1N HCl solution. Erythorbic acid was crystallized by concentration of the eluate in vacuum. The total yield of erythorbic acid recovery was 60%, probably due to decomposition during the concentration, which decomposition is facilitated by the HCl present.

In order to decrease this decomposition problem the selectivity of the anion exchanger was used for separation between the eluting HCl and the eluted erythorbic acid. A continuous extraction with a multi-bed resin system was used. Amberlite IR4B was found to be the most suitable weak base anion exchanger for that purpose. The eluant was 1NHCl and the regenerant was 2N NaOH solution. Using that system, recovery of 90.9% of crude crystals and 4.5% in a mother liquor were found. On recycle of HCl+ erythorbic acid containing solutions to the resin and on recystallization of the HCl free erythorbic acid solutions, a yield of 91.2% on the crude erythorbic acid content of the broth was achieved out of which 68.4% were in free acid form and 22.8% in sodium salt form.

The method of separation described consumes acids and bases and forms salts (NaCl in this particular case), as an undesired by-product. In the fermentation liquor the erythrobic is a mixture of the free acid form and a salt, depending on the final pH. Addition of Ba(OH)$_2$ according to the procedure suggested here, converts more of it into the salt form (using a barium salt instead of the base would avoid neutralization of free erythorbic acid, but would contaminate the solution with an anion of another acid). In the next stage all the erythorbate salt present in the solution is converted to the free acid form on a strong acid cation exchanger. More than one mole of a strong acid per mole of acidulated erythorbate are consumed for the regeneration of the cation exchanger. The erythorbic acid (free) containing solution is contacted with a weak base anion exchanger on which the acid is bound. On the elution of the adsorbed erythorbic acid more than one mole of HCl is adsorbed on the anion exchanger per mole of eluted erythorbic acid. Then at least one mole of base per mole of adsorbed HCl is used for the regeneration of the anion exchanger.

The recovery process described in the prior art thus suffers from several disadvantages. In order to separate erythorbic acid from the relatively dilute fermentation liquor at a reasonable concentration, it uses the chemical energy of the (indirect) neutralization of a mineral acid and mineral base (HCl and NaOH in the examples given above). As a result, costly reagents are consumed and an undesired salt is formed and there arises a need to dispose thereof. In addition, anions present in the fermentation liquor, mainly phosphate, are removed in a pretreatment, which could introduce traces of barium to the product and form barium salts which also require disposal. Cations present in the fermentation liquor are removed by strong acid cation exchangers, which also add to the salt production.

The present invention relates to a process for the separation of erythorbic acid which is more advantageous. Furthermore, this process avoids, or at least reduces to a minimum, the consumption of chemical energy of neutralization for such a separation.

SUMMARY OF THE INVENTION

With the above-described state of the art in mind, according to the present invention there is now provided a process for the recovery of erythorbic acid from an aqueous feed solution containing values of erythorbic acid at a concentration of less than 0.7 mol/kg, comprising adsorbing a major portion of said erythorbic acid with a solid phase adsorbent resin selected from resins carrying a pyridine function and resins of similar or weaker basicity; separating said erythorbic acid-containing resin from residual aqueous solution, and subjecting said erythorbic acid-containing resin to a desorbing operation with a neutral solvent at a temperature of at least 20° C. higher than the temperature at which said adsorption is carried out, whereby there is obtained a solution of erythorbic acid in solvent in which the concentration of erythorbic acid is at least equal to its concentration in said aqueous feed solution.

The basicity of water-soluble bases is determined by the pH of their solutions. That of water-immiscible bases (fatty amines, basic resins) cannot be measured directly. Their apparent basicity is determined by various methods having one element in common: the water-immiscible base is contacted with an acid-containing aqueous solution. The degree of acid transfer from the aqueous solution into the water-immiscible base, or more particularly, the pH of the aqueous solution in equilibrium with the base, shows the apparent basicity. A theoretical treatment is given in several articles, including "Basicities of Weak Base Ion Exchange Resins," by Gustafson, et al., *Ind. Eng. Chem. Fundam.*, Vol. 9, p. 221 (1970). The authors of this article have studied the basicity of several resins by equilibrating them with aqueous amine-amine hydrochloride buffer solutions, followed by determination of the degree of neutralization α of the resins as a function of the pH of the solution. As explained in the article, the pK of the resin is calculated from $$pK = pH - \log \alpha/(1-d)$$

Using this method for poly(2-methyl-5-vinylpyridine) cross-linked with 5, 7 and 10% divinylbenzene gave a pK of about 4.

Using other basicity measurement methods (for example, equilibration with HCl+NaCl solutions, as proposed by Nagasawa, et al., *Mem. Fac. Eng. Nagoya Univ.*, Vol. 10, p. 105 (1958) could result in different pK values for a particular resin. Yet, the relative basicities of resins can be determined by comparing their apparent basicity by one of the known methods. The resins suitable for the process of the present invention are those carrying a pyridine function and resins of similar, or weaker, basicity.

In preferred embodiments of the present invention, there is obtained a solution of erythorbic acid in solvent in which the concentration of erythorbic acid is higher than its concentration in said aqueous feed solution.

In the above process, at least 90% of said erythorbic acid is adsorbed by said solid phase adsorbent resin from said aqueous feed solution.

In preferred embodiments of the present invention, said solid phase resins are polyvinylpyridine polymers such as poly 2- and poly 4-vinylpyridine free base gel or macroreticular resins exhibiting a bead form. These resins are preferably at least about 2% cross-linked, and more preferably, at least about 8% crosslinked, with a suitable cross-linking agent, desirably divinylbenzene. More preferred resins to date have been 2% to 25% cross-linked, bead form poly 2- and poly 4-vinylpyridine polymers. For example, preferred polymers in work to date have been poly 2- and poly 4-vinylpyridine resins available from Reilly Industries, Inc., Indianapolis, Ind., in the REILLEX™ polymer series. These REILLEX™ polymers are 2% to 25% cross-linked, and exhibit good thermal stability and adsorptive and desorptive capacities and other preferred features as described herein.

The preferred resin beads can be of any suitable mesh size, for instance, from about 20 to about 60 mesh. Further, the resins can include a minor amount of functionalization of their pyridine groups, which minor amount can include, for example, functionalization to pyridine N-oxide or quaternary salt species. This functionalization has been incorporated to modify the relative basicity of the nonfunctionalized pyridine groups and thereby to modify their adsorptive and desorptive properties.

Kulprathipanja, in U.S. Pat. No. 4,720,579, proposes a process for separating citric acid from a fermentation broth by contacting with a polymeric adsorbent selected from the group consisting of an insoluble crosslinked polystyrene polymer and a non-ionic hydrophobic insoluble polyacrylic ester polymer at adsorption conditions selected to selectively adsorb said citric acid. In another patent, U.S. Pat. No. 4,851,573, Kulprathipanja proposes an adsorption process for separating citric acid from a fermentation broth by contacting with a water-insoluble, weakly basic, anionic exchange resin possessing tertiary amine or pyridine functional groups, at adsorption conditions selected to selectively adsorb said citric acid, desorbing said citric acid with a desorbent comprising water or a dilute inorganic acid at desorption conditions, said adsorption conditions including pH lower than the first ionization constant of citric acid. This patent directs a strong preference for desorption by a dilute sulfonic acid, because in some cases water is not strong enough to recover the adsorbed citric acid. Desorption with a neutral solvent at a temperature of at least 20° C. higher than the temperature at which the adsorption is carried out, is not claimed or exemplified. In fact, the second patent states, "Desorption conditions will include the same range of temperature and pressures as used for adsorption conditions."

U.S. Pat. No. 4,323,702 claims a process for recovering a carboxylic acid from an aqueous solution by adsorption on a polymeric material having a pyridine skeletal structure and a cross-linked structure, followed by desorption through the use of a desorption agent selected from the group consisting of an aliphatic alcohol, an aliphatic ketone, and a carboxylic ester. The list of suitable carboxylic acids (column 3, lines 24–39) does not include erythorbic acid, which is not a carboxylic acid. The examples use propionic acid, benzoic acid, phthalic acid, malonic acid, tartaric acid, adipic acid, citric acid, methacrylic acid and acetic acid, all of which are carboxylic acids and not lactones.

Said patent claims that the resin is effective, even if the temperature of adsorption is high (column 3, lines 53–55), teaching away from elution at elevated temperatures. Elution at a temperature higher than the adsorption temperature was not shown in the examples of said patent. Furthermore, methanol and acetone were used as the desorbing agents in the examples. A nearly complete recovery of the acid from its aqueous solution was not shown or claimed, particularly not with a resin after being used and eluted.

The invention of PCT Application No. WO 93/06226 is directed to an extractive fermentation of lactic acid, whereby broth is continuously removed from the fermentor, separated from the cells and passed through a polymer phase-containing pyridine group. The main goal is to maintain the pH and the lactate concentration in the fermentor at levels that reduce the product inhibition in the fermentor. Elution (desorption) of the adsorbed acid is very briefly referred to: "The adsorbed lactic acid can be recovered using a suitable desorbing agent. Suitable desorbing agents will include, for example, polar organic solvents such as alcohols (e.g., methanol) as well as hot water" (page 10, lines 19–22).

Example 6 of said PCT application uses 5% solutions of $NH_3$, $H_2SO_4$ or HCl for lactic acid desorption. Examples 2, 4 and 5 use methanol. No examples are given for the use of water for lactic acid desorption. No claim is made in said application to desorption at a temperature higher than that of the adsorption, or to obtaining the desorbed product at a temperature higher than that of the feed solution.

PCT Application WO 92/16490 relates to a process for recovering citric acid from a medium comprising it. In one preferred embodiment, the medium is contacted with a solid-phase, free base polymer having tertiary amine functions to adsorb citric acid, which is then desorbed by displacement with a strong acid, e.g., $H_2SO_4$ or HCl. In another preferred embodiment, the medium is contacted with a solid phase, free base polymer having pyridine functions at a temperature below about 40° C. to adsorb citric acid, which is then desorbed with hot water at a temperature of at least about 75° C. No claim is made to achieving a product at a concentration higher than that of the feed.

In Example 1 of said application, a 10% citric acid solution was passed through a polyvinylpyridine polymer resin until the resin was saturated. The resin was then rinsed with $CO_2$ saturated water, and then was washed with water at 85° C. The citric acid concentration in the aqueous solution obtained (desorbate) was not given in the example.

In Example 3, a polyvinylpyridine resin was used in processes as described in Example 1, and the collected desorbed fluids were put back into the column after another saturation and rinse cycle, instead of water. The internal column temperature was brought to at least 85° C. According to WO 92/16490, "Using that technique, a concentration of up to about 10% citric acid is achieved in two cycles. Additional cycles can be performed to further increase citric acid concentration, but in Applicant's work thus far, due to decreasing usable capacity of the resin with each cycle, the best efficiency has been achieved after two cycles." Thus, Example 3 teaches that in order to desorb citric acid at concentrations similar to those of the feed, desorbate should be recycled to desorption. As a result, the desorption is not completed and the resin loses capacity in the next cycle.

Another aspect that was not referred to in PCT WO 92/16490 is that of the completion of citric acid recovery from the broth. Any acid left there forms a product loss. No data is given in the examples on how complete the recovery is. Yet, it is clear that desorption with citric acid-containing solution not only decreases the resin's capacity, but also decreases the efficiency of citric acid recovery from the medium.

In fact, the Applicant of PCT Application WO 92/16490, Reilly Industries, Inc., together with Advanced Separation Technologies, Inc., optimized and piloted their process. The pilot program results, as published in October, 1994, show a product concentration of 10% citric acid, compared to a feed concentration of 15%. The recovery was 95% or higher. Therefore, these results teach that operating the process at conditions allowing high recovery of the acid, results in a product that is more dilute than the feed.

Erythorbic acid is not a carboxylic acid, and one could not draw analogies from other acids as to its behavior in adsorption on pyridine-based resins and in desorption. Yet, if such analogies could have been drawn, they would have indicated that product concentration on adsorption, followed by desorption at elevated temperature, is not attainable. An earlier publication by Reilly Industries, Inc. [Ernst and McQuigg, Paper No. 5AE, *AICHE National Meeting* (1992)] states: "The shape of the 250 equilibrium curve is quite favorable for adsorption . . . The 900 curve has the same shape, which is not favorable for stripping . . . The design, developed by Advanced Separations Technologies, Inc., indicates a product stream of 9% citric acid from a feed of 16% citric acid in broth."

The above statement is made for adsorption at 25° C. and desorption at 90° C. The upper limit of the temperature range is determined in the case of citric acid by the various partial vapor pressures, by the overall pressure in the system and by the thermal stability of the resin. One should keep in mind that in the case of erythorbic acid, there is an additional limitation. Erythorbic acid tends to oxidize. This oxidation could be enhanced by elevated temperatures and by the contact with the resin.

In a preferred embodiment said solvent used in said desorption step is selected from the group consisting of water alkanols, ketones and esters. In all these cases said solvent is essentially neutral and does not use a stripping acid as in the prior art.

In most cases at least part of the product is desired in free acid form. In those cases water is preferably used as said neutral solvent in said desorbing operation. When a part of the product is desired in a free acid form and another part of it in a form of a metal ion salt, part of the adsorbed acid is desorbed with water and another part with a solution comprising a base or a salt of said metal ion. In a preferred embodiment a solution comprising a base of the metal ion is used. Preferable the base is selected from a group consisting of hydroxides, bicarbonates, carbonates and mixtures thereof. More preferably said metal ion is an alkali metal ion, most preferably sodium.

It was found that in those cases where a part of the product is desired in a free acid form and another part in a form of a metal ion salt, a preferred combined process involves first desorbing erythorbic acid in acid form at the desired proportion by desorbing with water and then desorbing the rest with a solution comprising a base of the metal ion. Such a combination makes the desorbing with water more efficient. Thus, the temperature span between the adsorption temperature and that of the desorbing temperature could be smaller than in the case where all the adsorbed acid is desorbed with water. Alternatively, the same temperature span is used and the product of desorption with water is more concentrated. In such a preferred embodiment said desorption with a solution comprising a base of the metal ion can be effected at any convenient temperature, which does not need to be higher than that of adsorption.

In some cases the aqueous feed solution may consist of erythorbic acid, at least one erythorbate salt or mixtures thereof. The ratio between these constituents is determined by the pH of the solution. For those cases the term "erythorbic acid" would refer to the free acid form of said acid. Thus, in a preferred embodiment, at least 90% of the erythorbic acid present in said aqueous feed in the free acid form is adsorbed by said solid phase adsorbent resin.

In a preferred embodiment of the cases where the aqueous feed solution may consist of erythorbic acid, at least one erythorbate salt or mixtures thereof, erythorbate salts in said aqueous feed may be converted to erythorbic acid prior to said adsorption with said solid phase adsorbent resin, after such adsorption, simultaneously with said absorption or a combination thereof. In a preferred embodiment such conversion is effected prior to said adsorption and the newly formed erythorbic acid is co-adsorbed with the acid present there before. In another preferred embodiment the conversion is effected after the adsorption and the formed erythorbic acid is recovered by known means, preferably by adsorption on a resin. More preferably, the resin used for said recovery of erythorbic acid formed on the conversion of erythorbate salt is the same solid phase adsorbing resin as that used for the adsorption of the erythorbic acid content of said aqueous feed. In a further preferred embodiment the resin used for said recovery of erythorbic acid formed on the conversion of erythorbate salt is the resin formed on said desorption operation. In a most preferred embodiment said resin formed on said desorption operation is used for the recovery of erythorbic acid formed on the conversion of erythorbate salt and that resin is then used for the adsorption of the erythorbic acid content of said aqueous feed.

Said conversion of erythorbate salt to erythorbic acid is effected by methods known per se. An example for such conversion method is contacting said aqueous solution containing said salt with a water immiscible cation exchanger in its acid form, which cation exchanger could be in solid form, e.g., a resin, or liquid, e.g. a water immiscible organic acid. On such contact cations from said aqueous solution are adsorbed on- or extracted into the said water immiscible cation exchanger and protons are transferred into said aqueous solution forming erythorbic acid therein. In a preferred embodiment of using a liquid cation exchanger, the latter is contacted with said aqueous solution indirectly. An example for such indirect contact is the introduction of a membrane between the liquids. Preferably this membrane is a charged membrane, most preferably a cation exchange membrane.

Preferably said conversion of erythorbate salt to erythorbic acid is effected in a method that does not consume acids and bases as reagents and without rejecting salts into the environment. Such method comprises electrodialytic water splitting using bipolar membranes. In this method electric energy is used as the driving force for said conversion rather than chemical energy. Another method for using electric energy is to use acids and base, e.g. as in the case of conversion through ion exchange, and to decompose the byproduct salt formed back into the corresponding acid and base by electrolysis or by electrodialytic water splitting. Other conversion methods suitable for the present invention use $CO_2$ as an acidulant, directly or indirectly.

A preferred embodiment, for those cases where the erythorbic acid formed on said conversion is recovered by adsorption is conducting said adsorption simultaneously with said conversion. Such combined conversion and adsorption facilitates the conversion. Such combination enables using a water soluble acid as an acidulant, making use of the selectivity of the adsorbents used in separating between acids. Thus, an acid less preferred by the adsorbent than erythorbic acid (HX) is added to the solution consisting of said erythorbate salt. On contacting with the adsorbent, erythorbic acid is adsorbed on it and a salt of HX is formed. Alternatively, HX is introduced with the adsorbent.

In those cases where the conversion of erythorbate salts is combined with the adsorption of the erythorbic acid formed into a simultaneous operation, and where the composition of the adsorbing resin used is as defined for the present invention, said combined operation is considered the step of adsorbing of erythorbic acid in the invention.

In a preferred embodiment the erythorbic acid and the erythorbate salts, if present, are produced directly or indirectly by fermentation (i.e. erythorbic acid, erythorbic salts or a mixture thereof is the fermentation product, or is formed by the conversion of a fermentation product). In a further preferred embodiment the aqueous feed solution is a fermentation liquor. Such fermentation liquor is preferably treated prior to the adsorption step. Preferably such pretreatment consists of operations such as removal of biomass by methods known per se, e.g. centrifugation, filtration and membrane filtration. If desired, the solution is treated by an adsorbent such as an active carbon, diatomaceous earth or an adsorbing resin. Other pretreatments include ion exchange, solvent, extraction, etc.

In another preferred embodiment the aqueous feed is formed in an extractive fermentation. A solution out of the fermentor is transferred through said adsorbent resin to effect said adsorption step in which at least a part of the erythorbic acid present therein is adsorbed and the effluent is recycled to the fermentor, as is or after some treatment. In another preferred embodiment the acid in said solution out of the fermentor is adsorbed on a basic resin or extracted by a basic extractant. The basicity of those could be relatively high, if needed for efficient removal of the erythorbic acid from the solution, which is then recycled to the fermentor, as is or after some treatment. The adsorbed or extracted acid is stripped with a solution of a base to form a solution of an erythorbate salt, which forms the aqueous feed in the present invention, as is or after modification.

In U.S. Pat. No. 5,391770 ascorbic acid solutions in methanol or in methanol water solutions are purified by the use of ion-exchangers. The function of said ion exchangers is to bind impurities rather than to bind the abscorbic acid as can clearly be seen from step d of claim 1 of set patent which relates to "without absorption of the lactic acid . . . ". Thus said patent does not teach or suggest the process of the present invention.

In U.S. Pat. No. 2,443,583 there is described the separation of ascorbic acid by adsorption on an anion exchanger, followed by desorption with a solution of a strong acid. Thus, this patent is directed to the very process limitations avoided by the present invention, i.e. using an acid base neutralization (consumption of an acid and a base and formation of a salt) as a driving force for separation of the ascorbic acid.

U.S. Pat. No. 5,457,214 teaches the separation of erythorbic acid from photographic solutions. Anion-exchangers and cation exchangers are used for the removal of impurities, but not for the adsorption of erythorbic acid. The latter is separated from the purified solution by crystallization and thus said patent does not teach or suggest the process of the present invention.

Japanese Patent 40-27054 teaches an anion-exchange resin for used as a synthesis catalyst, but does not teach the same as a separation means and therefore also does not teach or suggest the process of the present invention.

Japanese Patent 40-21767 describes a process in which ascorbic acid is produced, using an anion exchanger as a catalyst. The product acid is adsorbed on the anion exchanger and then eluted by treatment with acid, alkali or inorganic salt (solutions). The process of said patent is different from the process of the present invention, in that there is no step of adsorbing ascorbic acid and in that the desorption is effected with acid and base solutions, while the present invention claims desorption with a neutral solution. Furthermore, said patent does not teach or suggest desorption at a temperature higher than that of adsorption, which is an essential feature of the present invention and desorption with a salt solution, as carried out in said patent, forms as a product a solution of ascorbate salt rathern than a solution of ascorbic acid, as formed according to the present invention.

Thus, as seen from the above discussion, the state of the art does not teach whether binding to the pyridine based resin and desorption at an elevated temperature is attainable without degradation of the erythorbic acid, and in fact, none of the above-mentioned publications teaches or suggests the process of the present invention.

As is well-known, a strong adsorbent is needed for high yield recovery from the feed solution. On the other hand, desorption is hindered by strong adsorbents, resulting in dilute desorbate solutions. The state of the art does not teach whether a pyridine based resin is strong enough to show high yields in adsorbing erythorbic acid from the dilute solutions and still weak enough to allow desorption at a concentration higher than its concentration in the feed.

While the invention will now be described in connection with certain preferred embodiments in the following example and with reference to the attached figure, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following example which includes preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Figure 1:
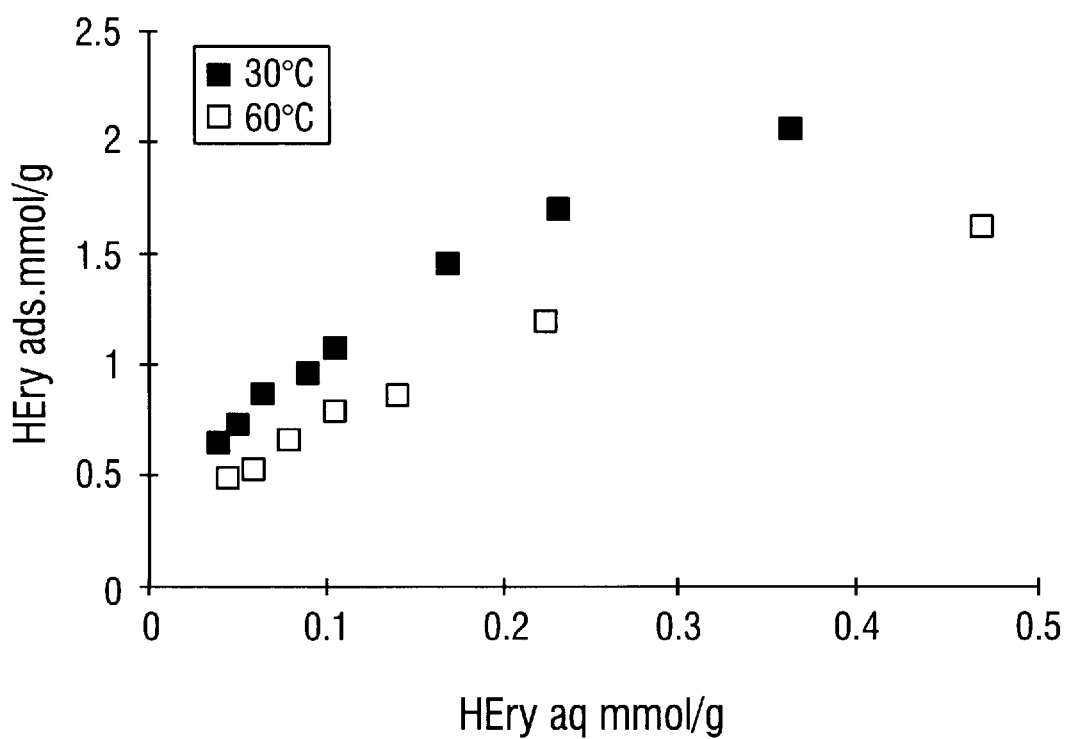
FIG. 1 represents the isotherms of erythorbic acid adsorption at different temperatures.

An aqueous solution comprising 7 g/l of erythorbic acid was contacted at 25° C. counter-currently with a series of columns, comprising Reillex™ 425 resin. The flow rate was 7 aqueous solution volumes per volume of resin, and the number of contacts was 7. More than 90% of the acid was adsorbed on the resin.

The resin was then washed at 80° C. counter-currently with water. Here again, 7 stages were used. Practically all the adsorbed erythorbic acid was recovered, at a concentration of 10 g/l.

FIG. 1 presents the isotherms of erythorbic acid adsorption on Reillex 425 at 30° C. and 60° C. The temperature effect is clearly seen—the adsorption at 60° C. is less efficient than that at 30° C. FIG. 1 also shows the favorable shape of the adsorption isotherms. Let the isotherm at 30° C. represent the adsorption of erythorbic acid. Adsorption efficiency is high starting at very low aqueous phase concentrations, as shown e.g. by resin loading of about 0.6 mmole/g in equilibrium with aqueous solution of about 0.05 mmole/g (distribution coefficient >10). The curve is slightly concaved, which ensures complete adsorption of the erythorbic acid in a small number of counter—current stages. Let the isotherm at 60° C. represent the desorption of erythorbic acid. While the desorption curve for citric acid, as found by the producer of the Reillex resins (Ernst and McQuibb), is strongly curved upward, that for erythorbic acid is slightly curved downward (and is even more so at somewhat higher temperatures), allowing for efficient stripping. Thus, as the producers of the resin found, their product provides for efficient adsorption, but is unfavorable for stripping. By analogy to liquid-liquid extraction with amine based extractants, one would expect citric acid to have the best combination of adsorption and stripping at higher temperature. It has now been surprisingly found that this combination for erythorbic acid is much better, providing for efficient adsorption and favorable stripping.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of erythorbic acid from an aqueous feed solution containing values of erythorbic acid at a concentration of less than 0.7 mol/kg, comprising:

adsorbing a major portion of said erythorbic acid with a solid phase adsorbent resin selected from resins carrying a pyridine function and resins of similar or weaker basicity;

separating said erythorbic acid-containing resin from residual aqueous solution, and subjecting said erythorbic acid-containing resin to a desorbing operation with a neutral solvent at a temperature of at least 20° C. higher than the temperature at which said adsorption is carried out, whereby there is obtained a solution of erythorbic acid in solvent in which the concentration of erythorbic acid is at least equal to its concentration in said aqueous feed solution.

2. A process according to claim 1, comprising passing said aqueous feed solution through at least one column containing said resin.

3. A process according to claim 1, comprising passing said aqueous feed solution through a series of columns in a counter-current mode.

4. A process according to claim 1, wherein said resin carries pyridine functions.

5. A process according to claim 1, wherein said neutral solvent is water.

6. A process according to claim 1, wherein said aqueous feed solution containing values of erythorbic acid is obtained by fermentation.

7. A process according to claim 1, comprising adsorbing at least 90% of said erythorbic acid from said aqueous feed solution with said solid phase adsorbent resin.

8. A process according to claim 1, in which there is obtained a solution of erythorbic acid in solvent in which the concentration of erythorbic acid is higher than its concentration in said aqueous feed solution.

9. A process for the recovery or erythorbic acid as claimed in claim 1, wherein erythorbic acid left on said adsorbent resin after said desorbing operation is desorbed with an aqueous solution of a base.

10. A process for the recovery of erythorbic acid as claimed in claim 9, wherein said base is selected from a group consisting of alkali metal hydroxides, bicarbonates and carbonates.

11. A process for the recovery of erythorbic acid as claimed in claim 1, wherein said aqueous feed solution consists of erythorbic acid, at least one erythorbate salt or mixtures thereof.

12. A process for the recovery of erythorbic acid as claimed in claim 11, wherein erythorbate salts in said aqueous feed are converted to erythorbic acid prior to said adsorption with said adsorbing resin.

13. A process for the recovery of erythorbic acid as claimed in claim 11, wherein erythorbate salts in said aqueous feed are converted to erythorbic acid after said adsorption with said adsorbing resin.

14. A process for the recovery of erythorbic acid as claimed in claim 11, wherein erythorbate salts in said aqueous feed are converted to erythorbic acid simultaneously with said adsorption with said adsorbing resin.

15. A process for the recovery of erythorbic acid as claimed in claim 12, wherein said conversion is conducted by a method selected from a group consisting of methods utilizing ion exchangers, extraction, $CO_2$ as an acidulant, charged membranes, electric energy and combinations thereof.

16. A process for the recovery of erythorbic acid as claimed in claim 13, wherein said conversion is conducted by a method selected from a group consisting of methods utilizing ion exchangers, extraction, $CO_2$ as an acidulant, charged membranes, electric energy and combinations thereof.

17. A process for the recovery of erythorbic acid as claimed in claim 14, wherein said conversion is conducted by a method selected from a group consisting of methods utilizing ion exchangers, extraction, $CO_2$ as an acidulant, charged membranes, electric energy and combinations thereof.

18. A process for the recovery of erythorbic acid as claimed in claim 1, wherein said aqueous feed solution is a fermentation liquor.

19. A process for the recovery of erythorbic acid as claimed in claim 18, wherein said fermentation liquor is pretreated prior to said adsorbtion step.

20. A process for the recovery of erythorbic acid as claimed in claim 19, wherein said pretreatment is an operation selected from a group consisting of biomass removal and treatment with an adsorbent, an ion exchanger and a solvent or a combination thereof.

21. A process for the recovery of erythorbic acid as claimed in claim 19, wherein said biomass removal is effected by membrane filtration.

22. A process for the recovery of erythorbic acid as claimed in claim 1, wherein said solvent used in said desorption step is selected from the group consisting of water, alkanols, ketones and esters.

* * * * *